(12) United States Patent
Kim et al.

(10) Patent No.: US 12,008,201 B2
(45) Date of Patent: Jun. 11, 2024

(54) DISPLAY DEVICE AND AN OPERATING METHOD THEREOF

(71) Applicant: Samsung Display Co., Ltd., Yongin-Si (KR)

(72) Inventors: Yuna Kim, Seoul (KR); Hee Seomoon, Seoul (KR); Soojung Lee, Suwon-si (KR); Seungwook Chun, Daegu (KR); Boram Choi, Asan-si (KR)

(73) Assignee: SAMSUNG DISPLAY CO., LTD., Yongin-Si (KR)

( * ) Notice: Subject to any disclaimer, the term of this patent is extended or adjusted under 35 U.S.C. 154(b) by 0 days.

(21) Appl. No.: 17/328,038

(22) Filed: May 24, 2021

(65) Prior Publication Data

US 2022/0066615 A1 Mar. 3, 2022

(30) Foreign Application Priority Data

Aug. 28, 2020 (KR) .................. 10-2020-0109534

(51) Int. Cl.
*G06F 3/041* (2006.01)
(52) U.S. Cl.
CPC ........ *G06F 3/04186* (2019.05); *G06F 3/0412* (2013.01); *G06F 3/0414* (2013.01)
(58) Field of Classification Search
None
See application file for complete search history.

(56) References Cited

U.S. PATENT DOCUMENTS

| 9,555,240 | B2 | 1/2017 | Choi et al. |
| 10,698,519 | B2 | 6/2020 | Park et al. |
| 2009/0066673 | A1* | 3/2009 | Molne ............... G06F 3/0418 345/178 |
| 2016/0041672 | A1* | 2/2016 | Hoen ................. G06F 3/041 345/173 |
| 2016/0349887 | A1* | 12/2016 | Wang ................ G06F 3/046 |
| 2017/0277323 | A1* | 9/2017 | Kim .................. G06F 3/0446 |
| 2018/0032195 | A1* | 2/2018 | Lee ................... G06F 3/0488 |
| 2018/0143669 | A1* | 5/2018 | Bok .................. G06F 1/1643 |
| 2018/0224963 | A1* | 8/2018 | Lee ................... G06F 3/017 |
| 2018/0361189 | A1* | 12/2018 | Gupta ............... A63B 24/0062 |
| 2019/0012029 | A1* | 1/2019 | Hong ................ G06F 3/047 |
| 2019/0114004 | A1* | 4/2019 | Lee ................... G06F 3/0418 |
| 2019/0302949 | A1* | 10/2019 | Ling ................. G06F 3/0488 |
| 2020/0026422 | A1 | 1/2020 | Seomoon et al. |

(Continued)

FOREIGN PATENT DOCUMENTS

| KR | 10-2017-0061560 | 11/2015 |
| KR | 10-1597624 | 2/2016 |

(Continued)

*Primary Examiner* — Christopher R Lamb
(74) *Attorney, Agent, or Firm* — F. Chau & Associates, LLC

(57) ABSTRACT

A display device including: a display panel; a first input sensor disposed on the display panel and configured to generate a first reception signal in response to a user input; a second input sensor spaced apart from the first input sensor on the display panel and configured to generate a second reception signal in response to the user input; and a readout circuit configured to generate an output signal corresponding to the user input in response to the first reception signal and the second reception signal.

17 Claims, 12 Drawing Sheets

(56) References Cited

U.S. PATENT DOCUMENTS

2020/0057507 A1  2/2020 Park et al.
2021/0126995 A1* 4/2021 Beckman .............. G06F 1/1626

FOREIGN PATENT DOCUMENTS

| KR | 10-1859670 | 5/2018 |
| KR | 10-2019-0039679 | 4/2019 |
| KR | 10-2020-0009164 | 1/2020 |
| KR | 10-2020-0019804 | 2/2020 |

* cited by examiner

DISPLAY DEVICE AND AN OPERATING METHOD THEREOF

CROSS-REFERENCE TO RELATED APPLICATION

This U.S. non-provisional patent application claims priority under 35 U.S.C. § 119 to Korean Patent Application No. 10-2020-0109534, filed on Aug. 28, 2020, the disclosure of which is incorporated by reference herein in its entirety.

TECHNICAL FIELD

The present inventive concept relates to a display device.

DISCUSSION OF THE RELATED ART

Multimedia electronic devices such as televisions, mobile phones, tablets, computers, navigation systems, game machines, and the like have display devices for displaying images. Electronic devices may include a touch-type display device capable of receiving a touch-based input that enables a user to intuitively and conveniently input information or commands.

Many personal electronic devices such as mobile phones utilize biometric information for user authentication; however, there is an increase in using a display device to provide biometric information to the user.

SUMMARY

An embodiment of the inventive concept provides a display device including: a display panel; a first input sensor disposed on the display panel and configured to generate a first reception signal in response to a user input; a second input sensor spaced apart from the first input sensor on the display panel and configured to generate a second reception signal in response to the user input; and a readout circuit configured to generate an output signal corresponding to the user input in response to the first reception signal and the second reception signal.

Each of the first input sensor and the second input sensor may be a pressure sensor.

The first input sensor may overlap a first side of the display panel, and the second input sensor may overlap a second side of the display panel.

The first input sensor may include: first input sensing cells; a first transmission line configured to transmit a transmission signal to the first input sensing cells; and first reception lines respectively connected to the first input sensing cells, each of the first reception lines configured to transmit a reception signal from the first input sensing cell to which it is connected, wherein the first transmission line and the first reception lines are electrically connected to the readout circuit.

Each of the first input sensing cells may include: a first electrode disposed on a substrate; a second electrode disposed on the substrate and spaced apart from the first electrode; and a pressure sensing layer directly disposed on the first electrode and the second electrode.

The first input sensor and the second input sensor may be spaced apart from each other in a first direction, and each of the first input sensing cells may be arranged in a second direction crossing the first direction.

The second input sensor may include: second input sensing cells; a second transmission line configured to transmit a transmission signal to the second input sensing cells; and second reception lines respectively connected to the second input sensing cells, each of the second reception lines configured to transmit a reception signal from the second input sensing cell to which it is connected, wherein the second transmission line and the second reception lines are electrically connected to the readout circuit.

The readout circuit may include: an analog to digital converter configured to convert the first reception signal received from the first input sensor and the second reception signal received from the second input sensor into a first digital reception signal and a second digital reception signal, respectively; a force calculation unit configured to convert the first digital reception signal and the second digital reception signal into a force signal; and a grip force calculation unit configured to convert the force signal into a grip force signal.

The force calculation unit may generate the force signal based on a sum or an average of the first digital reception signal and the second digital reception signal.

The readout circuit may further include a lookup table for storing the grip force signals corresponding to the force signals.

The readout circuit may detect a user's touch area based on the first reception signal from the first input sensor and the second reception signal from the second input sensor, and outputs the grip force signal corresponding to the user's grip force input when the touch area is greater than or equal to a preset area.

Each of the first input sensor and the second input sensor may be a resistance change type pressure sensor.

Resistance of each of the first input sensor and the second input sensor may decrease as external pressure increases.

The first input sensor and the second input sensor may be disposed on a rear surface of the display panel.

The display device may further include an input sensing layer including a first sensing area, a second sensing area and a third sensing area, wherein the display panel includes a display area overlapping the first sensing area, a first edge display area adjacent to a first side of the display area and overlapping the second sensing area, and a second edge display area adjacent to a second side of the display area and overlapping the third sensing area.

The first input sensor may correspond to the second sensing area of the input sensing layer, and the second input sensor may correspond to the third sensing area of the input sensing layer.

An embodiment of the inventive concept provides an operating method of a display device including a display panel and having a first input sensor and a second input sensor disposed on the display panel, the method including: receiving a first reception signal and a second reception signal from the first input sensor and the second input sensor, respectively; converting the first reception signal and the second reception signal into a first digital reception signal and a second digital reception signal, respectively; generating a force signal based on the first digital reception signal and the second digital reception signal; and converting the force signal into a grip force signal.

The method may further include detecting a touch area based on the first reception signal and the second reception signal, wherein the converting of the first reception signal and the second reception signal into the first digital reception signal and the second digital reception signal may be performed when the touch area is greater than or equal to a reference area.

Each of the first input sensor and the second input sensor may be a resistance change type pressure sensor.

The generating of the force signal may include generating the force signal based on a sum or an average of the first digital reception signal and the second digital reception signal.

An embodiment of the inventive concept provides a display device including: a display panel; a first input sensor arranged at a first side of the display panel; a second input sensor arranged at a second side of the display panel opposite the first side; and a readout circuit configured to detect a user's grip force in response to a first signal from the first input sensor and a second signal from the second input sensor.

The first input sensor may include a plurality of first pressure sensor cells and the second input sensor may include a plurality of second pressure sensor cells.

The readout circuit may include a force calculation circuit configured to generate a force signal in response to the first and second reception signals and a grip three calculation circuit configured to generate a grip force signal corresponding to the user's grip force based on the force signal.

The grip force calculation circuit may further generate the grip force signal based on a value corresponding to the force signal, the value being stored in a memory.

The memory may be a lookup table.

BRIEF DESCRIPTION OF THE FIGURES

The above and other features of the inventive concept will become more apparent by describing in detail embodiments thereof with reference to the accompanying drawings. In the drawings.

DETAILED DESCRIPTION OF THE EMBODIMENTS

Figure 1:
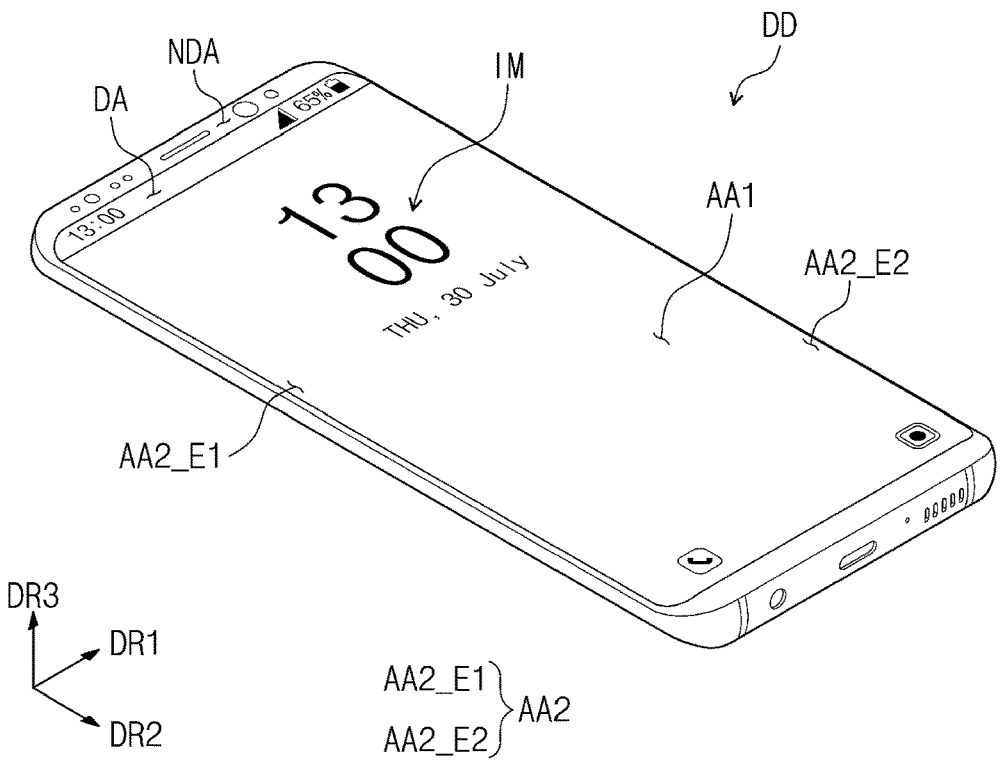
FIG. 1 is a perspective view of a display device according to an embodiment of the inventive concept.

In this specification, when an element (or region, layer, part, etc.) is referred to as being "on", "connected to", or "coupled to" another element, it may be directly placed on/connected to/coupled to other components, or a third component may be arranged between them.

Like reference numerals may refer to like elements. Additionally, in the drawings, the thicknesses, proportions, and dimensions of components may be exaggerated for effective description.

It will be understood that the terms "first" and "second" are used herein to describe various components but these components should not be limited by these terms. The above terms are used only to distinguish one component from another. For example, a first component may be referred to as a second component and vice versa. The terms of a singular form may include plural forms unless otherwise specified.

In addition, terms such as "below", "the lower side", "on", and "the upper side" are used to describe a relationship of configurations shown in the drawings. The terms are described as a relative concept based on a direction shown in the drawings and thus the inventive concept is not limited thereto.

Hereinafter, embodiments of the inventive concept will lie described with reference to the drawings.

Figure 2:
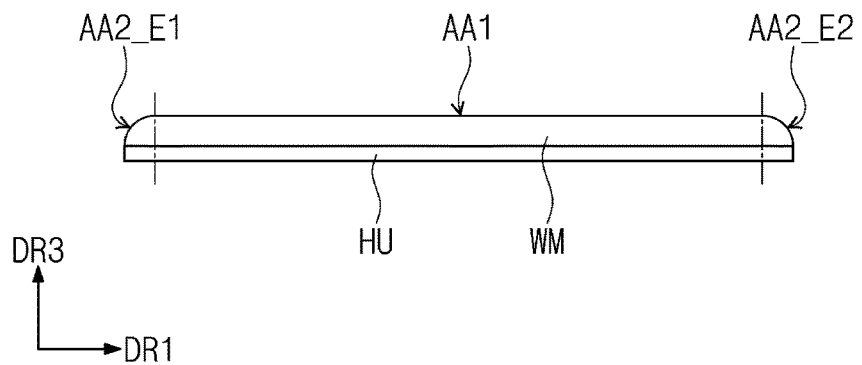
FIG. 2 is a side view of the display device illustrated in FIG. 1 as viewed from a second direction.

FIG. 1 is a perspective view of a display device according to an embodiment of the inventive concept. FIG. 2 is a side view of the display device illustrated in FIG. 1 as viewed from a second direction.

FIGS. 1 and 2 illustrate that a display device DD is a mobile phone. However, the inventive concept is not limited thereto, and the display device DD may be a small or medium-sized electronic device such as a tablet, a notebook computer, a car navigation device, a game machine, or a smart watch in addition to a large electronic device such as a television and a monitor.

Referring to FIGS. 1 and 2, in the present embodiment, a window WM and a housing HU are combined to form an appearance of the display device DD.

Active areas AA1 and AA2 in which an image IM is displayed and a non-display area NDA in which the image IM is not displayed may be included in the display device DD. In FIG. 1, as an example of the image IM, a date and time image (10:30, THU, 30 July) is shown in the active area AA1 of a display area DA.

The active areas AA1 and AA2 may include a first active area AA1 having a planar shape and a second active area AA2 bent from the first active area AA1. The second active area AA2 may form a curved edge of the display device DD. The second active area AA2 may be an area curved from the first active area AA1 with a predetermined curvature. However, the shape of the second active area AA2 is not limited thereto. For example, the second active area AA2 may be bent from the first active area AA1 and may have a planar shape that is inclined or perpendicular to the first active area AA1. The first and second active areas AA1 and AA2 are only geometrically divided areas, and may substantially implement one display surface. In other words, the first and second active areas AA1 and AA2 may be integrally formed. The non-display area NDA is an area in which the image IM is not displayed. The bezel area of the display device DD may correspond to the non-display area NDA. In addition, an image may not be displayed in a partial area of the second active area AA2. For example, a bezel area may be provided along an edge in the second active area AA2.

The first active area AA1 is parallel to a plane formed by a first direction. DIU and a second direction DR2. The normal direction of the first active area AA1, in other words, the thickness direction of the display device DD, may be parallel to the third direction DR3. The front (or upper) and rear (or lower) surfaces of the members of the display device DD may be demarcated by the third direction DR3. However, the directions indicated h the first direction DR1, to the second direction DR2, and the third direction DR3 are relative concepts and may be converted to other directions.

The second active area AA2 may be an area bent and extended from the first active area AA1. The second active area AA2 may include edge active areas AA2_E1 and AA2_E2 bent from sides of the first active area AA1. The second active area AA2 may include a first edge active area AA2_E1 bent from a first side of the first active area AA1 and a second edge active area AA2_E2 bent from a second side of the first active area AA1.

FIG. 1 illustrates that the second active area AA2 includes two edge active areas AA2_E1 and AA2_E2, but the inventive concept is not limited thereto. For example, the display device DD may include edge active areas that are bent at a short side and extended. In this case, the second active area AA2 may include three or four edge active areas.

Each of the first and second edge active areas AA2_E1 and AA2_E2 may be curved to have a predetermined curvature in the third direction DR3, Each of the first and second edge active areas AA2_E1 and AA2_E2 may have a short curved shape.

In an embodiment of the inventive concept, a first image displayed in the first active area AA1 and a second image displayed in the second active area AA2 may be dependent on each other. For example, a picture, a scene of a movie, or a user interface/user experience (UI/UX) design may be formed by a combination of the first image and the second image. The aesthetic feeling of the display device DD may be improved by the second active area AA2 bent to have a predetermined curvature, and thus, the area of the non-display area NDA recognized by the user may be reduced.

In an embodiment of the inventive concept, the first image displayed in the first active area AA1 and the second image displayed in the second active area AA2 may be independent of each other. For example, the first image may be a background picture and the second image may be an icon corresponding to an executable application of items for user convenience (e.g., power on/off, calls, messages, photo albums, music players, etc.).

The display device DD according to the embodiment of the inventive concept may detect an externally applied user's input. The user's input includes various types of external inputs such as part of the user's body, light, heat, or pressure. In addition, the display device DD may detect a user's input applied to the side or rear surface of the display device DD according to the structure of the display device DD.

Figure 3:
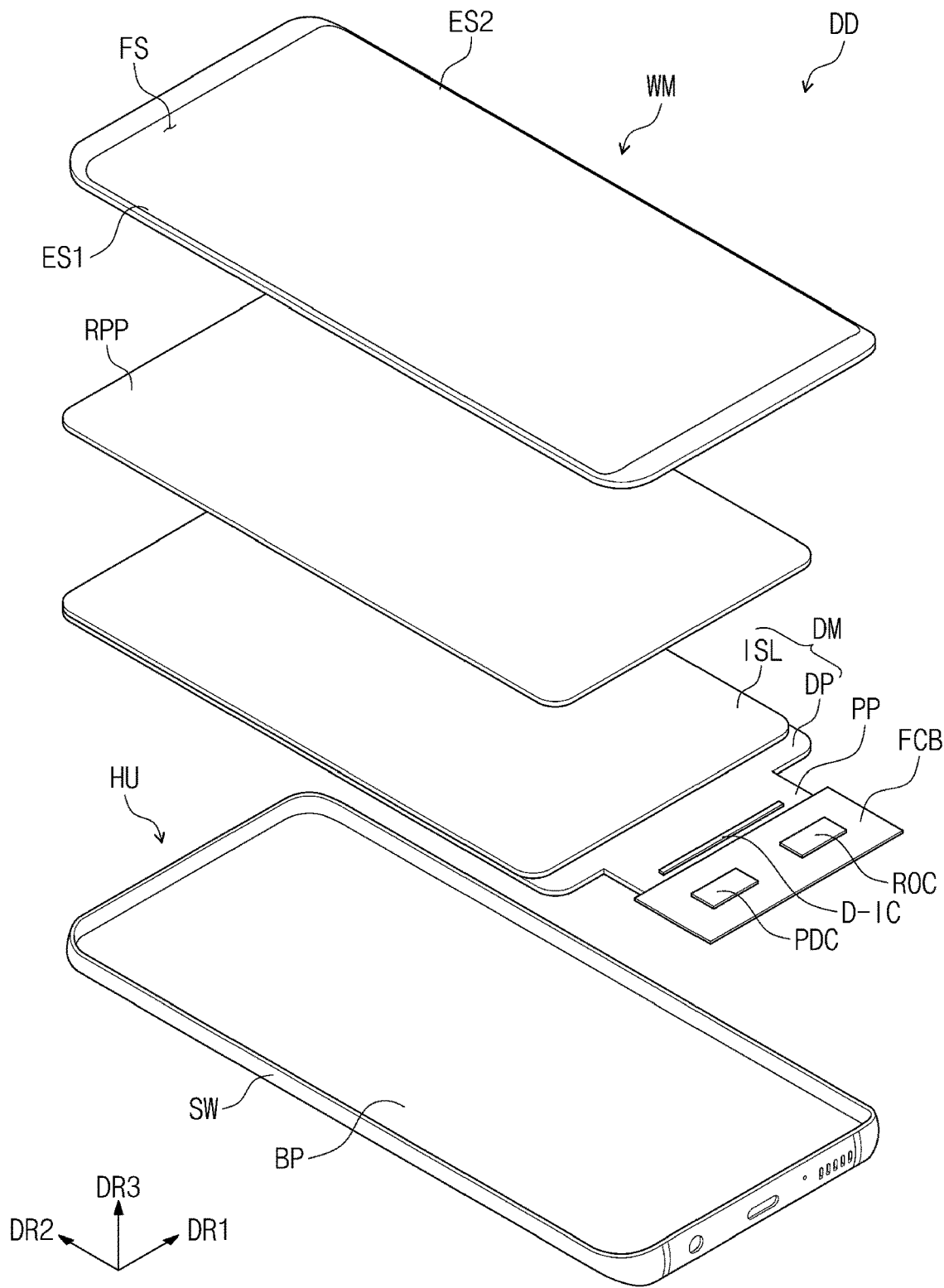
FIG. 3 is an exploded perspective view of a display device according to an embodiment of the inventive concept.

FIG. 3 is an exploded perspective view of a display device according to an embodiment of the inventive concept.

Referring to FIG. 3, the display device DD may include a window WM, an anti-reflection panel RPP, a display module DM, and a housing HU.

The window WM protects the upper surface of the display panel DP. The window WM may include an optically transparent insulating material. For example, the window WM may include glass or plastic. The window WM may have a multilayer structure or a single layer structure. For example, the window WM may include a plurality of plastic films bonded with an adhesive, or may include a glass substrate and a plastic film bonded with an adhesive.

The window WM may have a curved structure. The window WM may include a front part FS and one or more curved parts bent from the front part FS. Here, the front part FS and one or more curved parts may be referred to as a transmission part that transmits an image or light. The front part FS of the window WM may form a first active area AA1 (shown in FIG. 1) of the display device DD, and the one or more curved parts of the window WM may form a second active area AA2 (shown in FIG. 1).

As an example of the inventive concept, the window WM may include two curved parts, in other words, a first curved part ES1 and a second curved part ES2. In this embodiment, the front part FS may be a plane formed by the first direction DR1 and the second direction DR2. The front part FS may be perpendicular to the third direction DR3.

Each of the first curved part ES1 and the second curved part ES2 is bent from the front part FS. The first and second curved parts ES1 and ES2 may be bent from first and second sides of the front part FS, respectively. The first side and the second side of the front part FS may be parallel to the second direction DR2.

The first curved part ES1 and the second curved part ES2 may be bent from the front part FS at a predetermined curvature. As an example of the inventive concept, the first curved part ES1 and the second curved part ES2 may have the same curvature.

The anti-reflection panel RPP may be placed under the window WM. The anti-reflection panel RPP reduces the reflectance of external light incident from the upper side of the window WM. In one embodiment of the inventive concept, the anti-reflection panel RPP may be omitted or may be embedded in the display module DM.

The display module DM may display an image IM (see FIG. 1) and detect an external input. The display module DM includes an active area and a peripheral area. The active area may be an area activated according to an electrical signal.

In this embodiment, the active area is an area in which the image IM is displayed, and may be an area in which an external input is detected. The active area may include a first display area DA1 (see FIGS. 4A and 4B), a first edge display area DA2_E1 (see FIGS. 4A and 4B), and a second edge display area DA2_E2 (see FIGS. 4A and 4B).

The front part FS, the first curved part ES1, and the second curved part ES2 of the window WM overlap at least the active area. For example, the front part FS, the first curved part ES1, and the second curved part ES2 overlap the front surface or at least part of the active area. However, this is illustrated as an example, and in the active area, an area in which the image IM is displayed and an area in which an external input is detected may be separated from each other.

The peripheral area is adjacent to the active area. The peripheral area may surround the active area. A driving circuit or a driving wire for driving the active area may be disposed in the peripheral area.

In this embodiment, a part of the active area of the display module DM and a part of the peripheral area may be bent. The display module DM may be assembled in a partially curved state.

The display module DM may include a display panel DP, an input sensing layer ISL, and a driving circuit.

The display panel DP may generate the image IM. The image IM generated by the display panel DP is visually recognized by the user from the outside through the window WM.

The input sensing layer ISL detects an external input applied from the outside. For example, the input sensing layer ISL may detect an external input provided to the window WM.

The display panel DP may further include a pad area PP disposed in the peripheral area. A driving chip D-IC and pads may be disposed in the pad area PP of the display panel DP. The driving chip D-IC may provide a driving signal to the display panel DP. The driving chip D-IC may be mounted on the display panel DP. The display panel DP may be electrically connected to a printed circuit board FCB through pads. In an embodiment of the inventive concept, the driving chip D-IC may be mounted on the printed circuit board FCB.

The printed circuit board FCB may include various driving circuits for driving the display module DM or a connector for supplying power. In an embodiment of the inventive concept, the printed circuit board FCB may include a panel driving circuit PDC for driving the display panel DP and a readout circuit ROC for driving the input sensing layer ISL. Each of the panel driving circuit PDC and the readout circuit ROC may be formed as an integrated circuit and mounted on the printed circuit board FCB. In another embodiment of the inventive concept, the panel driving circuit PDC and the readout circuit ROC may be configured as one integrated circuit. The printed circuit board FCB may be a flexible printed circuit board FCB.

The housing HU includes a bottom part BP and a side wall SW. The side wall SW may extend from the bottom part BP. The housing HU may accommodate the display panel DP in an accommodation space formed by the bottom part BP and the side wall SW. The window WM may be coupled to the side wall SW of the housing HU. The side wall SW of the housing HU may support the edge of the window WM.

The housing HU may include a material having relatively high rigidity. For example, the housing HU may include a plurality of frames and/or plates made of glass, plastic, or metal, or a combination thereof. The housing HU may stably protect components of the display device DD accommodated in the internal space from external impact.

Figure 4A:
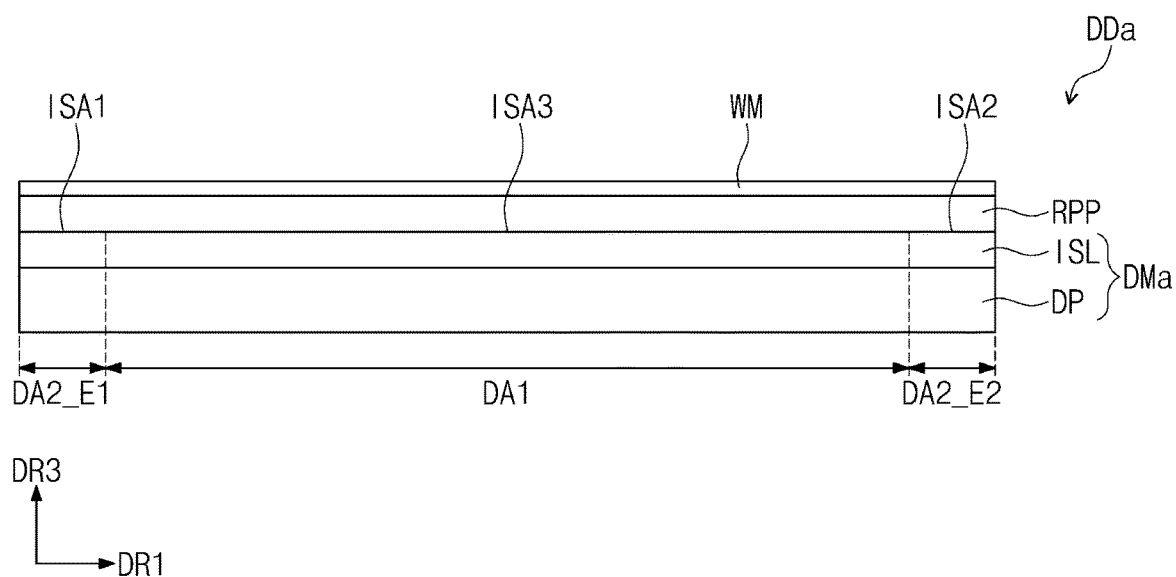
FIGS. 4A and 4B are cross-sectional views of a display device according to an embodiment of the inventive concept.
Figure 4B:
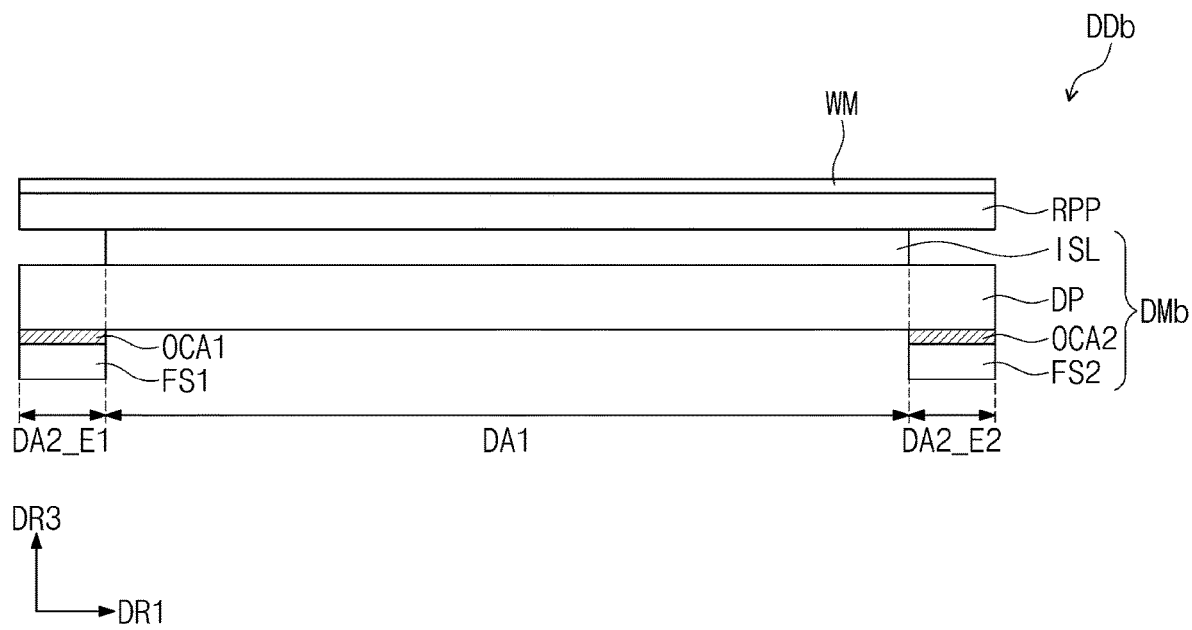

FIGS. 4A and 4B are cross-sectional views of a display device according to an embodiment of the inventive concept.

The display device DD shown in FIGS. 1 to 3 may be any one of a display device DDa shown in FIG. 4A and a display device DDb shown in FIG. 4B.

FIGS. 4A and 4B illustrate cross sections formed by the first direction DR1 and the third direction DR3. FIGS. 4A and 4B are schematically illustrated to explain the stacking relationship of functional members constituting the display devices DDa and DDb.

The display device DDa according to an embodiment of the inventive concept may include a display panel DP, an input sensing layer ISL, an anti-reflection panel RPP, and a window WM. The display panel DP, the input sensing layer ISL, the anti-reflection panel RPP and the window WM may be sequentially stacked. At least some of the components of the display panel DP, the input sensing layer ISL, the anti-reflection panel RPP, and the window WM may be formed by a continuous process, or at least some of the components may be bonded to each other through an adhesive member. The display panel DP and the input sensing layer ISL may constitute a display module DMa.

As illustrated in FIG. 4A, the input sensing layer ISL is directly disposed on the display panel DP. In the present specification, "the configuration of B is directly disposed on the configuration of A" may mean that a separate adhesive layer/adhesive member is not disposed between the configuration of A and the configuration of B. The configuration of B is formed through a continuous process on the base surface provided by the configuration of A after the configuration of A is formed.

The display panel DP generates an image, and the input sensing layer ISL obtains coordinate information of an external input (e.g., a touch or pressure event). The display module DMa according to an embodiment of the inventive concept may further include a protection member disposed on the lower surface of the display panel DP. The protection member and the display panel DP may be coupled through an adhesive member.

The display panel DP according to an embodiment of the inventive concept may be a light emitting display panel, but the inventive concept is not limited thereto. For example, the display panel DP may be an organic light emitting display panel or a quantum dot light emitting display panel. In the organic light emitting display panel, the light emitting layer may include an organic light emitting material. The light emitting layer of the quantum dot light emitting display panel may include a quantum dot, a quantum rod, and the like. Hereinafter, the display panel DP is described as the organic light emitting display panel.

The anti-reflection panel RPP reduces the reflectance of external light incident from the upper side of the window WM. An anti-reflection panel RPP according to an embodiment of the inventive concept may include a phase retarder and a polarizer. The phase retarder may be a film type or a liquid crystal coating type. The polarizer is also a film type, and may include a stretchable synthetic resin film. The phase retarder and the polarizer may further include a protective film. The phase retarder and the polarizer itself or a protective film may be referred to as a base layer of an anti-reflection panel RPP.

An anti-reflection panel RPP according to an embodiment of the inventive concept may include color filters. The color filters may have a predetermined arrangement. The arrangement of color filters may be determined in consideration of the emission colors of pixels included in the display panel DP. The anti-reflection panel RPP may further include a black matrix adjacent to the color filters.

The anti-reflection panel RPP according to an embodiment of the inventive concept may include a destructive interference structure. For example, the destructive interference structure may include a first reflective layer and a second reflective layer disposed on different layers. First reflected light and second reflected light reflected from the first reflective layer and the second reflective layer, respectively, may be destructively interfered by the destructive interference structure, and thus, reflectance of external light is reduced.

The window WM according to an embodiment of the inventive concept may include a glass substrate and/or a synthetic resin film. An optically transparent adhesive member may be disposed between the window WM and the anti-reflection panel RPP. In addition, an optically transparent adhesive member may be disposed between the anti-reflection panel RPP and the input sensing layer ISL.

In addition, in an embodiment of the inventive concept, each of the input sensing layer ISL, the anti-reflection panel RPP, and the window WM shown in FIG. 4A may be formed in a continuous process on a base surface provided to the display panel DP. In another embodiment of the inventive concept, the input sensing layer ISL, the anti-reflection panel RPP, and the window WM may be formed separately and coupled by an optically transparent adhesive member.

The display module DMa includes a first display area DA1 corresponding to the active area AA1 shown in FIG. 1, and a first edge display area DA2_E1 and a second edge display area DA2_E2 respectively corresponding to the first edge active area AA2_E1 and the second edge active area AA2_E2. The first edge display area DA2_E1 and the second edge display area DA2_E2 may be referred to as a first side and a second side, respectively.

In FIG. 4A, the first display area DA1, the first edge display area DA2_E1, and the second edge display area DA2_E2 of the display module DMa are illustrated to be flat, but the first edge display area DA2_E1 and the second edge display area DA2_E2 may be bent from the first display area DA1, respectively.

The input sensing layer ISL may include a first sensing area ISA1 corresponding to the first edge display area DA2_E1, a second sensing area ISA2 corresponding to the second edge display area DA2_E2, and a third sensing area ISA3 corresponding to the first display area DA1. For example, the first sensing area ISA1 may overlap the first edge display area DA2_E1, the second sensing area ISA2 may overlap the second edge display area DA2_E2 and the third sensing area ISA3 may overlap the first display area DA1. The first sensing area ISA1 and the second sensing area ISA2 of the input sensing layer ISL may detect not only a user's touch input but also a pressure input.

The display device DDb illustrated in FIG. 4B may include a display panel DP, an input sensing layer ISL, an anti-reflection panel RPP, and a window WM. The display panel DP, the input sensing layer ISL, the anti-reflection panel RPP, and the window WM shown in FIG. 4B are the same as or similar to the display panel DP, the input sensing layer ISL, the anti-reflection panel RPP, and the window WM shown in FIG. 4A, and thus redundant descriptions are omitted.

The display module DMb of the display device DDb illustrated in FIG. 4B further includes a first input sensor FS1, a second input sensor FS2, a first adhesive member OCA1, and a second adhesive member OCA2.

The first input sensor FS1 may overlap the first edge display area DA2_E1 of the display module DMb, and the second input sensor FS2 may overlap the second edge display area DA2_E2 of the display module DMb. A gap may be formed between the first input sensor FS1 and the second input sensor FS2 in the first display area DA1.

The first input sensor FS1 and the second input sensor FS2 may be disposed on a rear surface (e.g., a surface opposite to the display surface on which an image is displayed) of the display panel DP. The first adhesive member OCA1 may be disposed between the display panel DP and the first input sensor FS1, and the second adhesive member OCA2 may be disposed between the display panel DP and the second input sensor FS2. Each of the first adhesive member OCA1 and the second adhesive member OCA2 may be an optically transparent adhesive member.

Each of the first input sensor FS1 and the second input sensor FS2 may be a force sensor for detecting a user's pressure input.

In the example shown in FIG. 4B, the input sensing layer ISL may overlap the first display area DA1. In other words, in FIG. 4B the input sensing layer ISL may not overlap the first edge display area DA2_E1 and the second edge display area DA2_E2. In this case, an empty space may be provided between a portion of the display panel DP and a portion of the anti-reflective panel RPP in both of the first edge display area DA2_E1 and the second edge display area DA2_E2. In another embodiment of the inventive concept, the input sensing layer ISL may overlap at least one of the first edge display area DA2_E1 and the second edge display area DA2_E2 as well as the first display area DA1.

Figure 5:
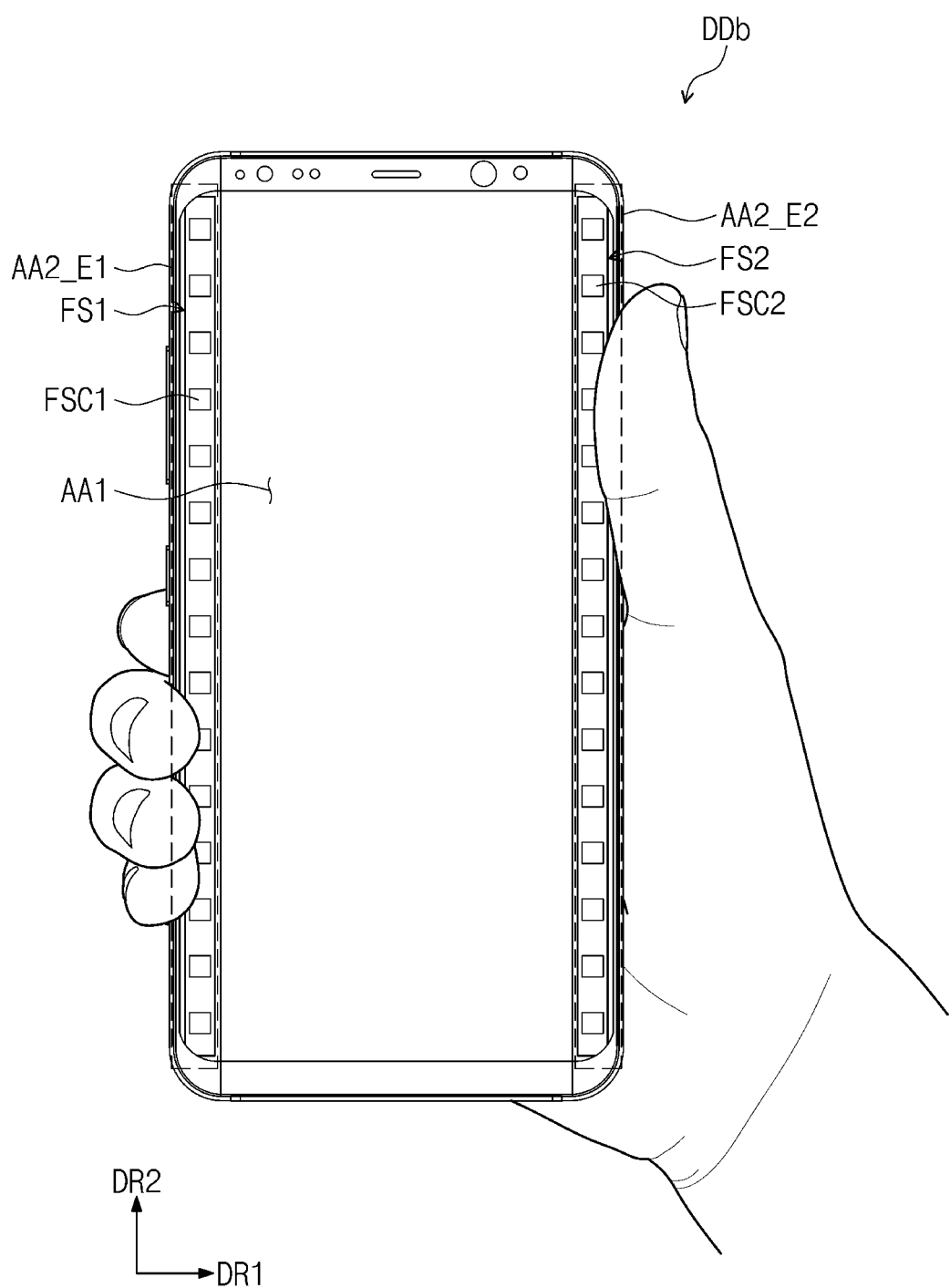
FIG. 5 is a plan view of a display device including a first input sensor and a second input sensor according to an embodiment of the inventive concept.

FIG. 5 is a plan view of the display device DDb including a first input sensor FS1 and a second input sensor FS2 according to an embodiment of the inventive concept.

Referring to FIG. 5, the first input sensor FS1 may overlap the first edge active area AA2_E1, and the second input sensor FS2 may overlap the second edge active area AA2_E2. The first input sensor FS1 and the second input sensor FS2 are provided on first and second sides of the display device DDb, respectively. For example, the first input sensor FS1 may extend along almost the entire first side of the display device DDb and the second input sensor FS2 may extend along almost the entire second side of the display device DDb.

The first input sensor FS1 may include a plurality of first pressure sensing cells FSC1 as first input sensing cells, and the second input sensor FS2 may include a plurality of second pressure sensing cells FSC2 as second input sensing cells. The first pressure sensing cells FSC1 may be spaced apart from each other in the second direction DR2. A space between adjacent first pressure sensing cells FSC1 may be greater than the size of an individual first pressure sensing cell FSC1, but the inventive concept is not limited thereto. The second pressure sensing cells FSC2 may be spaced apart from each other in the second direction DR2. A space between adjacent second pressure sensing cells FSC2 may be greater than the size of an individual second pressure sensing cell FSC2, but the inventive concept is not limited thereto.

When the user grabs the display device DDb with one hand, some or all of the first pressure sensing cells FSC1 may be touched, and some or all of the second pressure sensing cells FSC2 may be touched.

Figure 6:
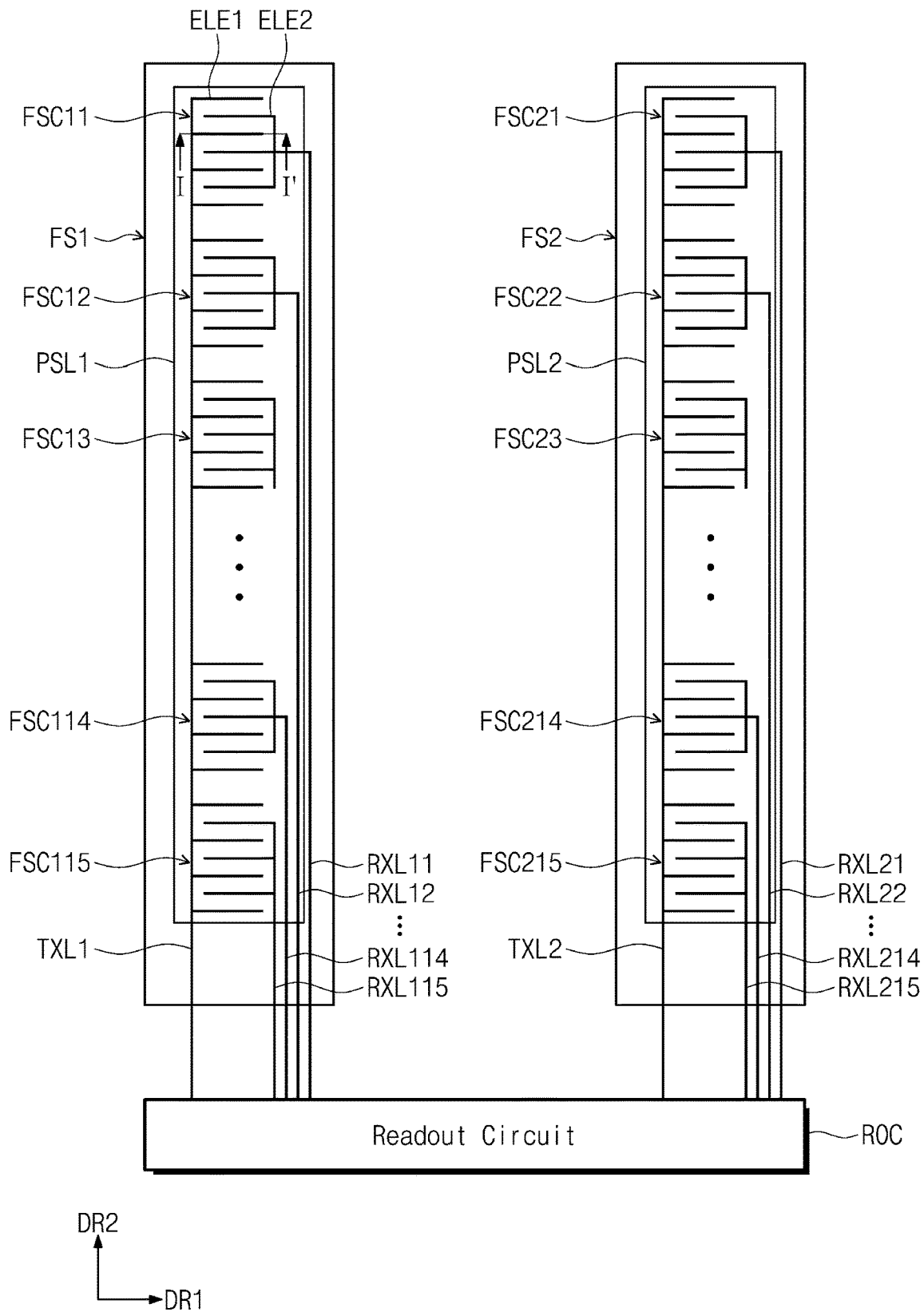
FIG. 6 is a diagram illustrating an electrical connection between a first input sensor and a second input sensor and a readout circuit according to an embodiment of the inventive concept.
Figure 7:
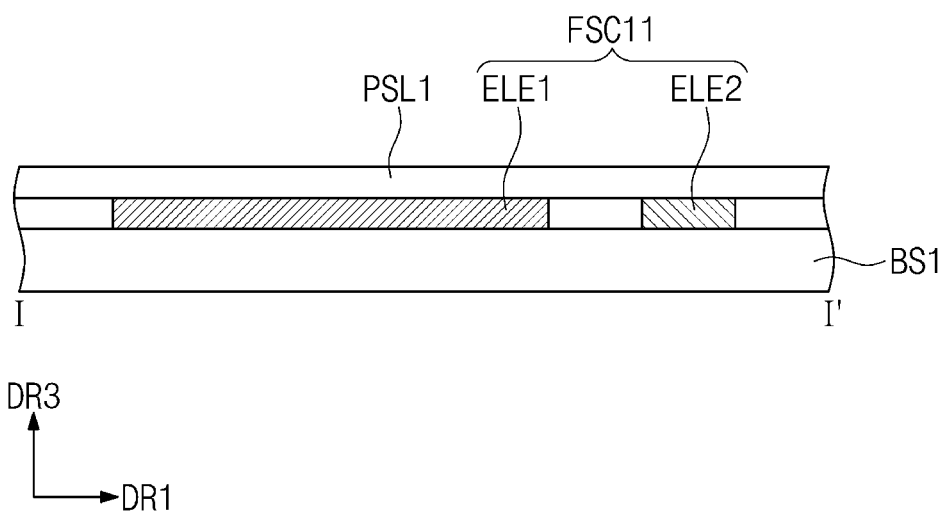
FIG. 7 is a cross-sectional view taken along line I-I' shown in FIG. 6.

FIG. 6 is a diagram illustrating an electrical connection between a first input sensor FS1 and a second input sensor FS2 and a readout circuit ROC according to an embodiment of the inventive concept. FIG. 7 is a cross-sectional view taken along line I-I' shown in FIG. 6.

Referring to FIGS. 6 and 7, the first input sensor FS1 includes a first base substrate BS1, first pressure sensing cells FSC11, FSC12, FSC13, . . . , FSC114 and FSC115 (referred as FSC11 to FSC 115), a first pressure sensing layer PSL1, a first transmission line TXL1, and first reception lines RXL11, RXL12, . . . , RXL114 and RXL115. The second input sensor FS2 may include a second base substrate, second pressure sensing cells FSC21, FSC22, FSC23, . . . , FSC214 and FSC215, a second pressure sensing layer PSL2, a second transmission line TXL2, and second reception lines RXL21, RXL22, . . . RXL214 and RXL215 (referred as RXL21 to RXL215). The first pressure sensing cells FSC11 to FSC115 may be arranged in a line in the second direction DR2, and the second pressure sensing cells FSC21 to FSC215 may be arranged in a line in the second direction DR2.

FIG. 7 shows only a cross section of the first pressure sensing cell FSC11, but the first pressure sensing cells FSC12 to FSC115 and the second pressure sensing cells FSC21 to FSC215 may have the same or similar structure as the first pressure sensing cell FSC11.

The first pressure sensing cell FSC11 includes a first electrode ELE1 and a second electrode ELE2. The first electrode ELE1 and the second electrode ELE2 are formed on the first base substrate BS1. The first electrode ELE1 and the second electrode ELE2 are spaced apart from each other. In an embodiment of the inventive concept, an insulating layer may be disposed between the first electrode ELE1 and the second electrode ELE2. In other words, by disposing an insulating layer on the first base substrate BS1, etching the insulating layer, and forming a conductive layer, a first electrode ELE1 and a second electrode ELE2 may be formed.

The first electrode ELE1 and the second electrode ELE2 may have a comb shape alternately disposed in the second direction DR2. For example, the first electrode ELE1 may include a plurality of sub-electrodes disposed between adjacent sub-electrodes of the second electrode ELE2. The pressure sensitivity of the first pressure sensing cell FSC11 may be increased by the first electrode ELE1 and the second electrode ELE2 having a comb shape.

The first electrode ELE1 and the second electrode ELE2 are made of a transparent conductive material such as Indium Tin Oxide (ITO), or may be formed of one or more materials selected from the group consisting of low-resistance metallic materials, for example, molybdenum (Mo), silver (Ag), titanium (Ti), copper (Cu), and aluminum (Al). The first electrode ELE1 and the second electrode ELE2 are disposed on the same layer. In addition, the first electrode ELE1 and the second electrode ELE2 may be disposed on the same layer and with the same material as the first transmission Line TXL1 and the first reception lines RXL11 to RXL115. However, the inventive concept is not limited thereto, and the first electrode ELE1 and the second electrode ELE2 may be disposed on a different layer from the first transmission line TXL1 and the first reception line. RXL11 to RXL115.

The first pressure sensing layer PSL1 is disposed on the first electrode ELE1 and the second electrode ELE2. The first pressure sensing layer PSL1 may be directly disposed on the first electrode ELE1 and the second electrode ELE2 to be electrically connected to the first electrode ELE1 and the second electrode ELE2, respectively. The first pressure sensing layer PSL1 may include a pressure sensitive material reacting to an external pressure. In FIG. 6, each of the first pressure sensing layer PSL1 and the second pressure sensing layer PSL2 is shown to have a quadrangular shape, but the inventive concept is not limited thereto. For example, each of the first pressure sensing layer PSL1 and the second pressure sensing layer PSL2 may be variously implemented as a polygon such as a rhombus, a triangle, and a hexagon, a circle, and an ellipse.

The size of the first pressure sensing cell FSC11 including the first electrode ELE1 and the second electrode ELE2 may be about 5×5 mm. Although it is shown in FIG. 6 that the first input sensor FS1 includes 15 first pressure sensing cells FSC11 to FSC115, and the second input sensor FS2 includes 15 second pressure sensing cells FSC21 to FSC215, the inventive concept is not limited thereto. Depending on the length of the display device DDb in the second direction DR2 (see FIG. 5), the size and number of each of the first pressure sensing cells FSC11 to FSC115 and the second pressure sensing cells FSC21 to FSC215 may be determined.

When a contact pressure is applied from the user, the first pressure sensing layer PSL1 may transmit the transmit signal received through the first transmission line TXL1 to the first reception lines RXL11 to RXL115. The first reception lines RXL11 to RXL115 may provide the receive signal received through the first pressure sensing layer PSL1 to the readout circuit ROC.

In addition, when a contact pressure is applied from the user, the second pressure sensing layer PSL2 may transmit the transmit signal received through the second transmission line TXL2 to the second reception lines RXL21 to RXL215. The second reception lines RXL21 to RXL215 may provide the receive signal received through the second pressure sensing layer PSL2 to the readout circuit ROC.

FIG. 6 illustrates that the first input sensor FS1 includes one first transmission line TXL1 and 15 first reception lines RX11 to RX115, but the inventive concept is not limited thereto. For example, the first input sensor FS1 may include a plurality of first transmission lines and a first reception line, or may include a plurality of first transmission lines and a plurality of first reception lines.

The readout circuit ROC may drive the first input sensor FS1 and the second input sensor FS2. In addition, the readout circuit ROC may drive the input sensing layer ISL shown in FIG. 4A and the input sensing layer ISL shown in FIG. 4B.

In a muscle mass measurement mode, the readout circuit ROC may output transmit signals to the first transmission line TXL1 and the second transmission line TXL2, respectively, and may receive receive signals from the first reception lines RXL11 to RXL115 and the second reception lines RXL21 to RXL215, respectively.

Figure 8:
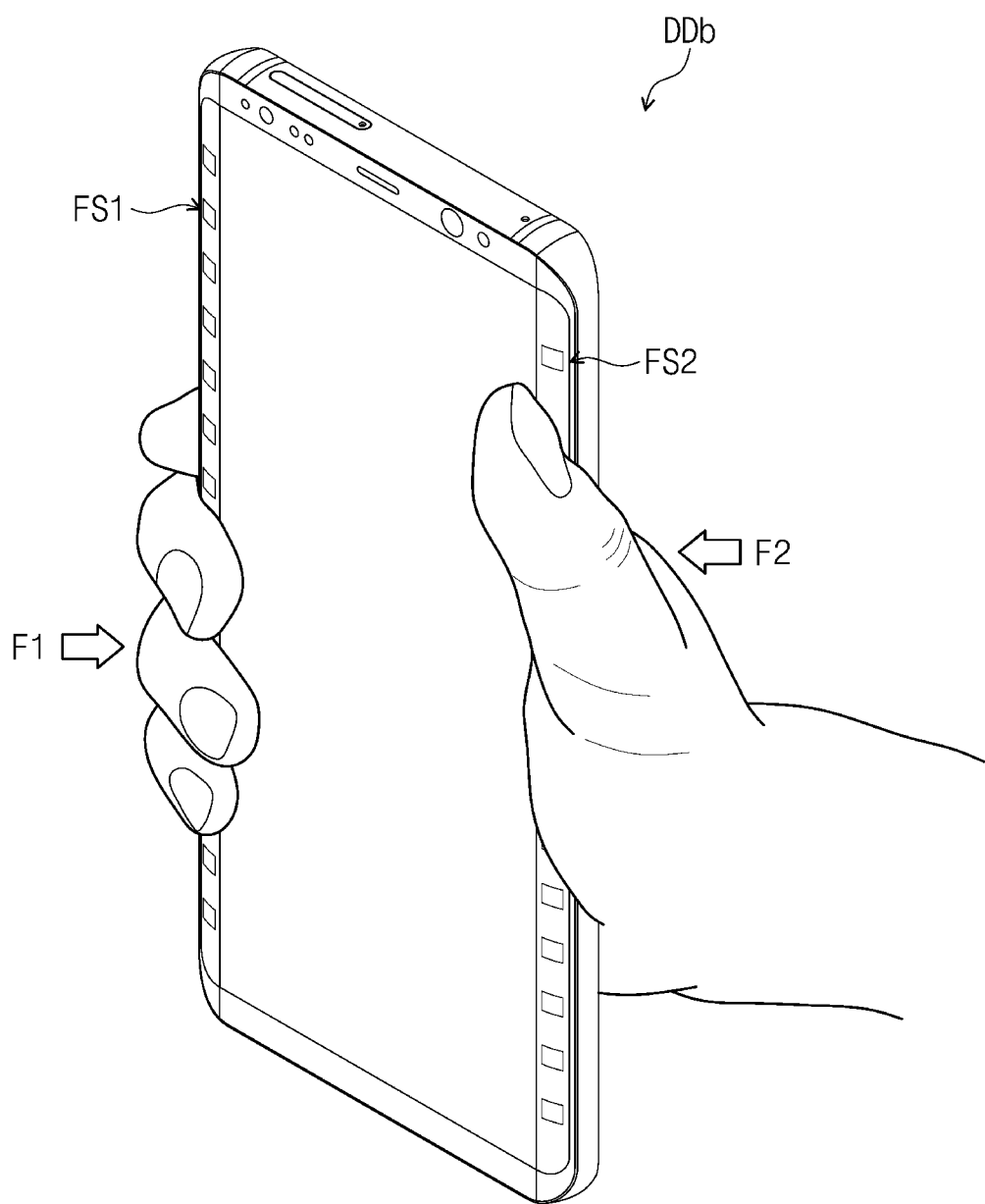
FIG. 8 is a perspective view illustrating a method of measuring muscle mass by a user using the display device according to an embodiment of the inventive concept.

FIG. 8 is a perspective view illustrating a method of measuring muscle mass by a user using the display device DDb according to an embodiment of the inventive concept.

Referring to FIG. 8, the user may hold the display device DDb with one hand in a form surrounding the display device DDb. A part of the thumb and a part of the palm of the user may contact some of the second pressure sensing cells FSC21 to FSC215 (refer to FIG. 6) of the second input sensor FS2. In addition, four fingers other than the user's thumb may contact some of the first pressure sensing cells FSC11 to FSC115 (refer to FIG. 6) of the first input sensor FS1.

According to the force (e.g., grip force) that the user holds the display device DDb, the pressure according to a first force F1 is transmitted to some of the first pressure sensing cells FSC11 to FSC115, and the pressure according to a second force F2 may be transmitted to some of the second pressure sensing cells FSC21 to FSC215.

Figure 9:
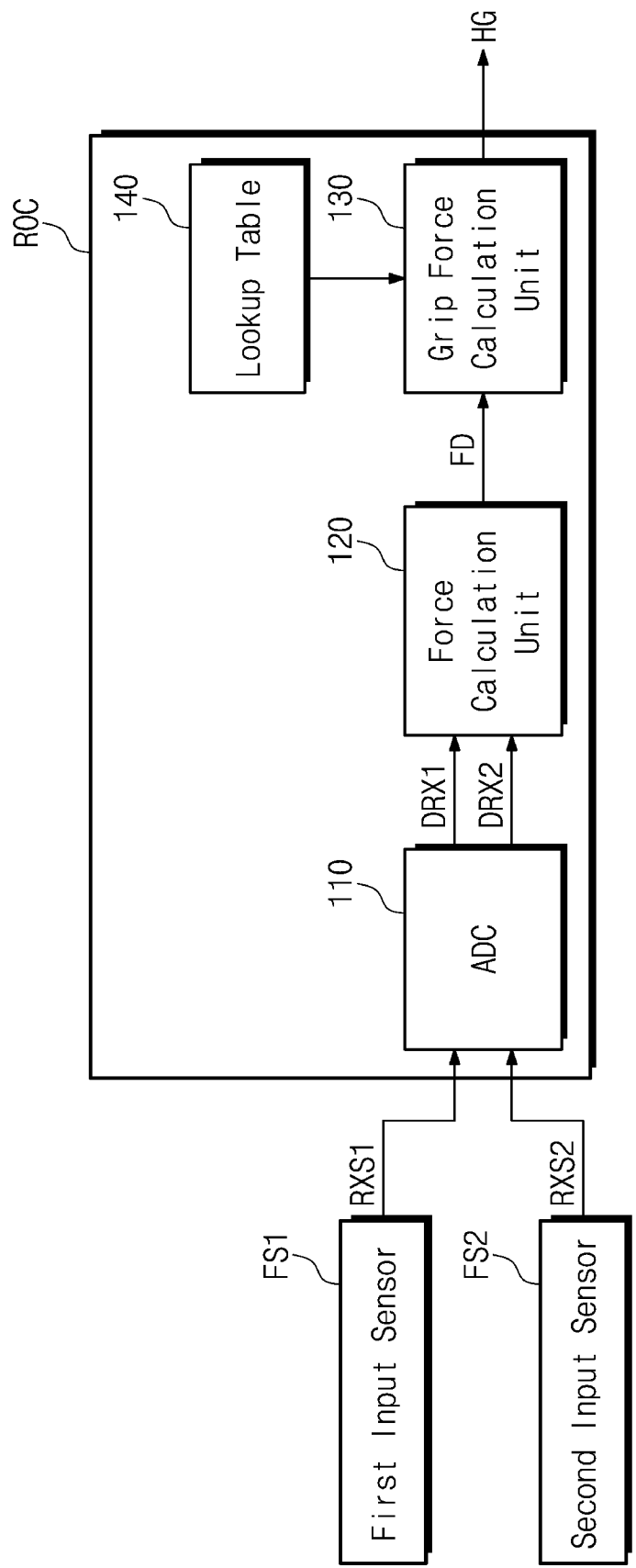
FIG. 9 is a block diagram illustrating a configuration of a readout circuit of a display device according to an embodiment of the inventive concept.

FIG. 9 is a block diagram illustrating a configuration of a readout circuit ROC of a display device according to an embodiment of the inventive concept.

Referring to FIG. 9, the readout circuit ROC includes an analog to digital converter ADC 110, a force calculation unit 120, a grip force calculation unit 130, and a lookup table 140.

The analog to digital converter ADC 110 receives a first reception signal RXS1 from the first reception lines RXL11 to RXL115 of the first input sensor FS1, and receives a second reception signal RXS2 from the second reception lines RXL21 to RXL215 of the second input sensor FS2.

Figure 10:
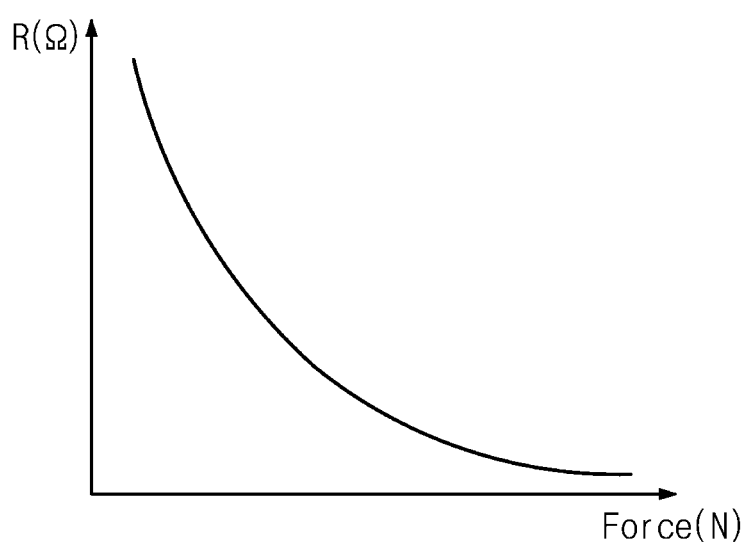
FIG. 10 is a graph showing a change in resistance according to a user's grip force or force.

FIG. 10 is a graph showing a change in resistance $R(\Omega)$ according to a user's grip force or force N.

The first pressure sensing layer PSL1 of the first input sensor FS1 and the second pressure sensing layer PSL2 of the second input sensor FS2 shown in FIGS. 6 and 7 are deformed, such as being compressed or stretched when subjected to pressure, and due to this deformation, resistances of the first pressure sensing layer PSL1 and the second pressure sensing layer PSL2 may be changed.

For example, the transmit signal provided to the first electrode ELE1 of the first pressure sensing cell FSC11 is transmitted to the second electrode ELE2 through the first pressure sensing layer PSL1, and depending on the resistance of the first pressure sensing layer PSL1, the current or voltage level of the receive signal outputted from the second electrode ELE2 may vary.

In the example shown in FIG. 10, the first pressure sensing layer PSL1 maintains a resistance value of a predetermined level when there is no pressure, and the resistance may decrease as the strength of the pressure increases.

In other words, the resistance of the first pressure sensing layer PSL1 and the second pressure sensing layer PSL2 is changed by the user's grip force, and current or voltage levels of the first reception signal RXS1 and the second reception signal RXS2 may change according to the changed resistance.

Referring to FIG. 9 again, the analog to digital converter ADC 110 converts the first reception signal RXS1 and the second reception signal RXS2, which are analog signals of current or voltage, into a first digital reception signal DRX1 and a second digital reception signal DRX2.

The force calculation unit 120 may convert the first digital reception signal DRX1 and the second digital reception signal DRX2 from the analog to digital converter ADC 110 into a force signal FD. For example, the force calculation unit 120 may calculate the sum or average of the first digital reception signal DRX1 and the second digital reception signal DRX2, and may output a force signal FD corresponding to the calculated sum or average. The force calculation unit 120 may be implemented by a circuit.

Figure 11A:
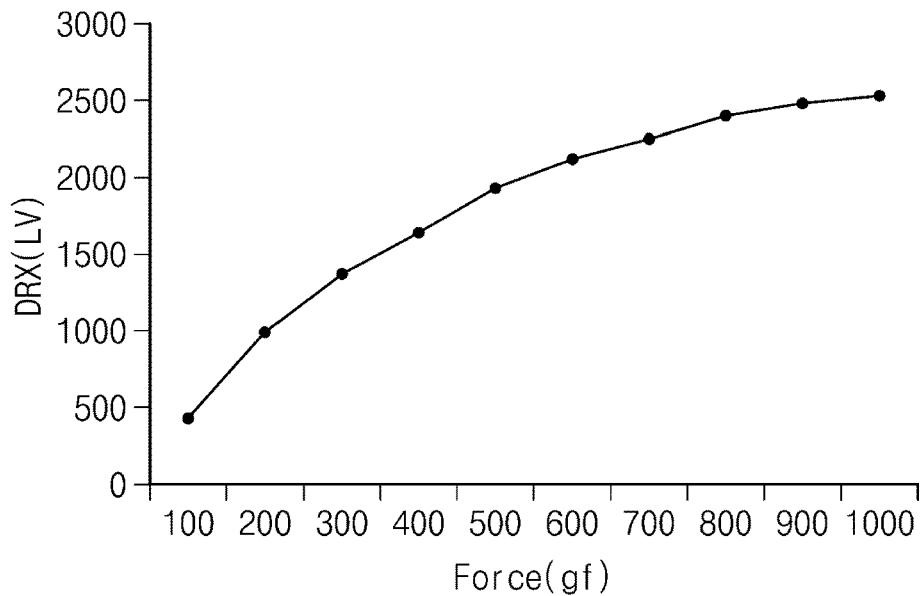
FIGS. 11A and 11B are graphs showing a relationship between a force and a reception signal calculated by a force calculation unit according to an embodiment of the inventive concept.
Figure 11B:
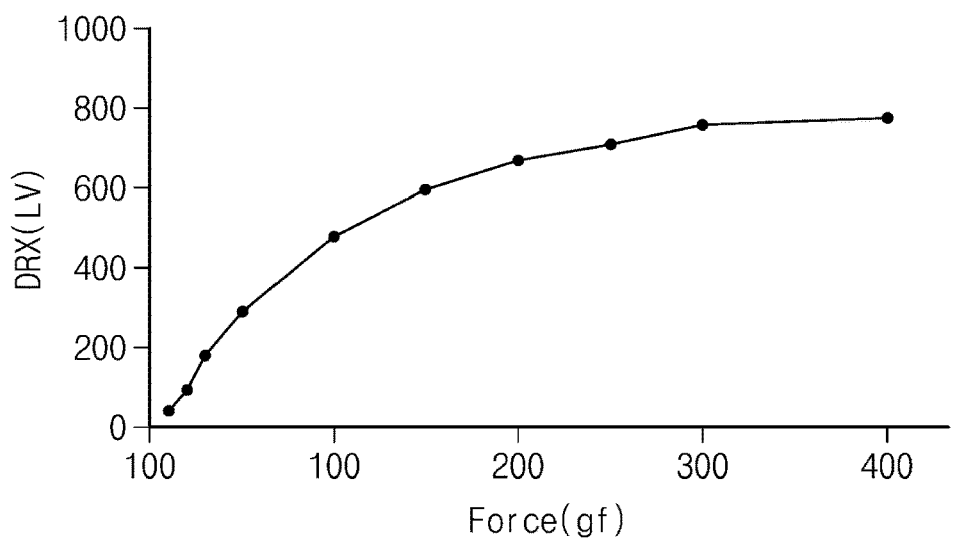

FIGS. 11A and 11B are graphs showing a relationship between a force and a reception signal calculated by a force calculation unit according to an embodiment of the inventive concept.

The vertical axes of the graphs shown in FIGS. 11A and 11B are the digital signal levels LV of the reception signal. DRX obtained by calculating the sum or average of the first digital reception signal DRX1 and the second digital reception signal DRX2 outputted from the analog to digital converter ADC 110 shown in FIG. 9, and the horizontal axes are the forces (gf).

FIG. 11A shows a case where the window WM shown in FIG. 3 is a glass substrate, and FIG. 11B shows a case where the window WM is a synthetic resin film.

In other words, depending on the material of the window WM, the correlation between the reception signal DRX and the force may be variously changed.

Referring to FIG. 9 again, the force calculation unit 120 may convert the first digital reception signal DRX1 and the second digital reception signal DRX2 into a force signal FD, but consider an external condition, for example, the material of the window WM.

The grip force calculation unit 130 may convert the force signal FD into a grip force signal HG by referring to the lookup table 140. The grip force calculation unit 130 may be implemented by a circuit.

Figure 12:
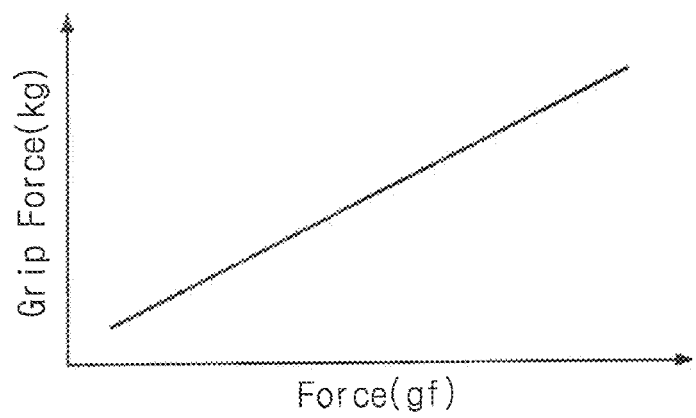
FIG. 12 is a graph showing the relationship between force and grip force.

FIG. 12 is a graph showing the relationship between force and grip force.

In FIG. 12, the horizontal axis represents force (gf) or force signal FD, and the vertical axis represents grip force (kg) or grip force signal HG.

As shown in FIG. 12, the force and the grip force may have a proportional relationship. For example, the force and grip force may have a relationship of H=aF+b. Here, H may be a grip force, F may be a force, and a and b may be preset constants.

Referring to FIG. 9 again, the lookup table 140 may store a grip force signal HG corresponding to the force signal FD. The grip force calculation unit 130 may read the grip force signal HG corresponding to the force signal FD from the lookup table 140.

Sarcopenia is a disease in which muscle mass, muscle strength, and muscle function are lower than a certain standard due to chronic diseases caused by aging, lack of nutrition, and decreased amount of exercise. One of methods to determine a user's health is to measure muscle mass. However, a separate measuring device is typically used to measure muscle mass.

The user's grip force is correlated with muscles such as the forearm muscles, and in general, as the muscle mass is larger, the grip force becomes stronger. In an embodiment of the inventive concept, the display device DD (refer to FIG. 1) may output a grip force signal HG corresponding to a user's grip force based on the pressure detected by the first input sensor FS1 and the second input sensor FS2 disposed in the first edge active area AA2_E1 and the second edge active area AA2_E2.

In FIGS. 4B to 9, it has been described as an example that each of the first input sensor FS1 and the second input sensor FS2 is a variable resistance pressure sensor (resistance change type pressure sensor) but the inventive concept is not limited thereto. For example, in FIG. 4B, the readout circuit ROC may detect a change in capacitance detected in the first edge display area DA2_E1 and the second edge display area DA2_E2 of the display module DMb to output a grip force signal HG corresponding to the user's grip force.

The grip force signal HG from the readout circuit ROC may be provided to the panel driving circuit PDC (refer to FIG. 3). The panel driving circuit PDC may display grip force information corresponding to the grip force signal HG on the display panel DP.

In another embodiment of the inventive concept, each of the first input sensor FS1 and the second input sensor FS2 may be a sensor using a piezoelectric semiconductor. The first input sensor FS1 and the second input sensor FS2 are not limited to the examples described in this specification and may be variously changed.

According to an embodiment of the inventive concept shown, for example, in FIGS. 4B, 5, 6 and 9, the display device DDb may include: a display panel DP; a first input sensor FS1 disposed on the display panel DP and configured to generate a first reception signal RXS1 in response to a user input; a second input sensor FS2 spaced apart from the first input sensor FS1 on the display panel DP and configured to generate a second reception signal RXS2 in response to the user input; and a readout circuit ROC configured to generate an output signal HG corresponding to the user input in response to the first reception signal RXS1 and the second reception signal RXS2.

Figure 13:
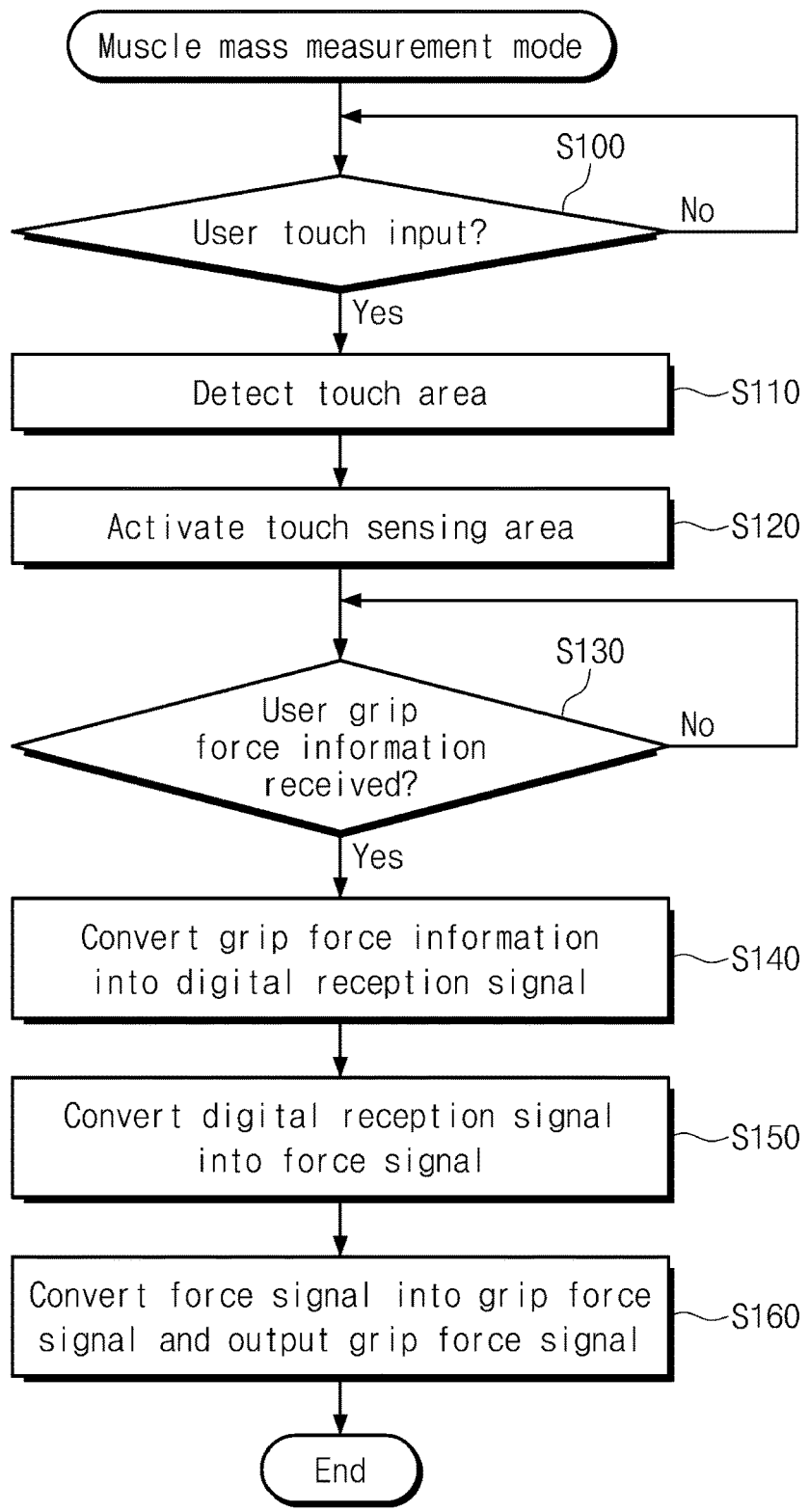
FIG. 13 is a flowchart illustrating an operation in a muscle mass measurement mode of a display device according to an embodiment of the inventive concept.

FIG. 13 is a flowchart illustrating an operation in a muscle mass measurement mode of a display device according to an embodiment of the inventive concept.

For convenience of description, a method of operating a display device according to an embodiment of the inventive concept will be described with reference to FIGS. 6 and 7, but the method of operating the display device is not limited thereto.

Referring to FIGS. 6, 9, and 13, the display device DDb may enter a muscle mass measurement mode according to a user's selection of an application program. The readout circuit ROC of the display device DDb detects a user touch input (or a user input) when the muscle mass measurement mode is started (operation S100).

When a user touch input is detected, the readout circuit ROC detects the touch area (operation S110), in other words, the area gripped by the user's hand. The readout circuit ROC may obtain the touch area based on the first reception signals RXS1 received from the first pressure sensing cells FSC11 to FSC115 of the first input sensor FS1, and the second reception signals RXS2 received from the second pressure sensing cells FSC21 to FSC215 of the second input sensor FS2.

The readout circuit ROC starts measuring the user's grip force when a predetermined number or more cells among the first pressure sensing cells FSC11 to FSC115 and the second pressure sensing cells FSC21 to FSC215 detect pressure. Accordingly, the user's muscle mass may be accurately measured.

If a touch input is detected using cells of less than the predetermined number among the first pressure sensing cells FSC11 to FSC115 and the second pressure sensing cells FSC21 to FSC215 (e.g., if the touch area is less than a preset area), the readout circuit ROC transmits an error message signal to the panel driving circuit PDC (refer to FIG. 3). The panel driving circuit PDC may display a message requesting a user's hand position to change on the display panel DP in response to the error message signal.

If a touch input is detected using cells of more than the predetermined number among the first pressure sensing cells FSC11 to FSC115 and the second pressure sensing cells FSC21 to FSC215 (e.g., if the touch area is greater than or equal to the preset area), the readout circuit ROC activates the touch sensing area (operation S120). In other words, the readout circuit ROC prepares to receive signals from the first pressure sensing cells and the second pressure sensing cells in which a touch input is detected among the first pressure sensing cells FSC11 to FSC115 and the second pressure sensing cells FSC21 to FSC215 in the touch sensing area.

In this case, receive signals from the first pressure sensing cells and the second pressure sensing cells in which a touch input is not detected among the first pressure sensing cells FSC11 to FSC115 and the second pressure sensing cells FSC21 to FSC215 may be excluded. In other words, the readout circuit ROC may not be provided with these signals. Accordingly, the grip force may be accurately measured.

The readout circuit ROC receives a first reception signal RXS1 from the first pressure sensing cells and a second reception signal RXS2 from the second pressure sensing cells in the touch sensing area so that a user may receive grip force information. If the user moves a part of a finger and the receive signal is not received from some of the first pressure sensing cells and the second pressure sensing cells in the touch sensing area, or the receive signal is lower than a reference level, the readout circuit ROC transmits an error message signal to the panel driving circuit PDC. The panel driving circuit PDC may display a message informing the user that the grip force is being measured on the display panel DP (refer to FIG. 3) in response to the error message signal.

When the first reception signal RXS1 and the second reception signal RXS2 corresponding to the user grip force information are normally received from the first pressure sensing cells and the second pressure sensing cells in the touch sensing area (operation S130), the readout circuit ROC may convert the grip force information into a digital reception signal (operation S140).

The analog to digital converter ADC 110 in the readout circuit ROC receives a first reception signal RXS1 from the first reception lines RXL11 to RXL115 of the first input sensor FS1, and receives a second reception signal RXS2 from the second reception lines RXL21 to RXL215 of the second input sensor FS2. The analog to digital converter ADC 110 converts the first reception signal RXS1 and the second reception signal RXS2, which are analog signals of current or voltage, to a first digital reception signal DRX1 and a second digital reception signal DRX2, which are digital signals.

The force calculation unit 120 in the readout circuit ROC converts the first digital reception signal DRX1 and the second digital reception signal DRX2 from the analog to digital converter ADC 110 into a force signal FD (operation S150).

The grip force calculation unit 130 converts the force signal FD into a grip force signal HG by referring to the lookup table 140 (operation 160). The grip force signal HG may be outputted to the panel driving circuit PDC (see FIG. 3).

When the first reception signal RSX1 from the first pressure sensing cells FSC11 to FSC115 and the second reception signal RSX2 from the second pressure sensing cells FSC21 to FSC215 are received for a predetermined time or longer, the readout circuit ROC may output a grip force signal HG corresponding to at least one of an average grip force, a minimum grip force, and a maximum grip force during the reception time.

A display device according to embodiments of the inventive concept may measure a grip force corresponding to a user's touch input using an input sensor provided in the display panel. Accordingly, the display device may improve user convenience by providing biometric information such as muscle mass information as well as a display function.

Although the embodiments of the inventive concept have been described, it is to be understood that the inventive concept should not be limited to these embodiments but various changes and modifications may be made by one of ordinary skill in the art.

What is claimed is:

1. A display device, comprising:
   a display panel;
   a first input sensor disposed on a first side of the display panel and configured to generate a first reception signal in response to a user input;
   a second input sensor spaced apart from the first input sensor on the first side of the display panel and configured to generate a second reception signal in response to the user input;
   a first adhesive member disposed between the first side of the display panel and the first input sensor;
   a second adhesive member disposed between the first side of the display panel and the second input sensor;
   a readout circuit configured to generate an output signal corresponding to the user input in response to the first reception signal and the second reception signal; and
   a window overlapping the display panel,
   wherein the readout circuit comprises:
   an analog to digital converter configured to convert the first reception signal received from the first input sensor and the second reception signal received from the second input sensor into a first digital reception signal and a second digital reception signal, respectively;
   a force calculation unit configured to convert the first digital reception signal and the second digital reception signal into a force signal based on one of a sum and an average of the first digital reception signal and the second digital reception signal;
   a lookup table for storing a grip force signal corresponding to the force signal; and a grip force calculation unit configured to convert the force signal into the grip force signal based on the lookup table, wherein a correlation between one of a sum and an average of the first digital reception signal and the second digital reception signal and the force signal is determined depending on a material of the window, wherein the display device further comprises:

an input sensing layer disposed on a second side of the display panel; and an anti-reflective layer disposed on the input sensing layer, wherein an empty space exists where the anti-reflective layer overlaps the first input sensor or the second input sensor since the input sensing layer is not in an area of the first and second input sensors, wherein an edge of the input sensing layer, an edge of the first input sensor and an edge of the first adhesive member contact a line that extends through the display panel and is perpendicular to top and bottom surfaces of the display panel.

2. The display device of claim 1, wherein each of the first input sensor and the second input sensor is a pressure sensor.

3. The display device of claim 1, wherein the first input sensor overlaps a first edge of the display panel, wherein the second input sensor overlaps a second edge of the display panel.

4. The display device of claim 1, wherein the first input sensor comprises:

first input sensing cells;

a first transmission line configured to transmit a transmission signal to the first input sensing cells; and first reception lines respectively connected to the first input sensing cells, each of the first reception lines configured to transmit a reception signal from the first input sensing cell to which it is connected, wherein the first transmission line and the first reception lines are electrically connected to the readout circuit.

5. The display device of claim 4, wherein each of the first input sensing cells comprises:

a first electrode disposed on a substrate;

a second electrode disposed on the substrate and spaced apart from the first electrode; and a pressure sensing layer directly disposed on the first electrode and the second electrode.

6. The display device of claim 4, wherein the first input sensor and the second input sensor are spaced apart from each other in a first direction, wherein each of the first input sensing cells is arranged in a second direction crossing the first direction.

7. The display device of claim 1, wherein the second input sensor comprises:

second input sensing cells;

a second transmission line configured to transmit a transmission signal to the second input sensing cells; and second reception lines respectively connected to the second input sensing cells, each of the second reception lines configured to transmit a reception signal from the second input sensing cell to which it is connected, wherein the second transmission line and the second reception lines are electrically connected to the readout circuit.

8. The display device of claim 1, wherein the readout circuit detects a user's touch area based on the first reception signal from the first input sensor and the second reception signal from the second input sensor, and outputs the grip force signal corresponding to a user's grip force input when the touch area is greater than or equal to a preset area.

9. The display device of claim 1, wherein each of the first input sensor and the second input sensor is a resistance change type pressure sensor.

10. The display device of claim 9, wherein resistance of each of the first input sensor and the second input sensor decreases as external pressure increases.

11. The display device of claim 1, wherein the first input sensor and the second input sensor are disposed on a rear surface of the display panel.

12. The display device of claim 1, wherein the input sensing layer includes a first sensing area, a second sensing area and a third sensing area, wherein the display panel comprises a display area overlapping the third sensing area, a first edge display area adjacent to a first side of the display area and overlapping the first sensing area, and a second edge display area adjacent to a second side of the display area and overlapping the second sensing area.

13. The display device of claim 12, wherein the first input sensor corresponds to the first sensing area of the input sensing layer, wherein the second input sensor corresponds to the second sensing area of the input sensing layer.

14. A display device, comprising:

a display panel;

a first input sensor arranged at a first side of the display panel;

a second input sensor arranged at the first side of the display panel;

a first adhesive member disposed between the first side of the display panel and the first input sensor;

a second adhesive member disposed between the first side of the display panel and the second input sensor;

a readout circuit configured to detect a user's grip force in response to a first signal from the first input sensor and a second signal from the second input sensor, wherein the first input sensor includes a plurality of first pressure sensor cells and the second input sensor includes a plurality of second pressure sensor cells, wherein each of the first and second pressure sensor cells comprises:

a first electrode disposed on a substrate;

a second electrode disposed on the substrate and spaced apart from the first electrode; and a pressure sensing layer directly disposed on the first electrode and the second electrode, wherein the first electrode and the second electrode each have a comb shape, wherein the display device further comprises:

an input sensing layer disposed on a second side of the display panel; and an anti-reflective layer disposed on the input sensing layer, wherein an empty space exists where the anti-reflective layer overlaps the first input sensor or the second input sensor since the input sensing layer is not in an area of the first and second input sensors, wherein an edge of the input sensing layer, an edge of the first input sensor and an edge of the first adhesive member contact a line that extends through the display panel and is perpendicular to top and bottom surfaces of the display panel.

15. The display device of claim 14, wherein the readout circuit includes a force calculation circuit configured to generate a force signal in response to first and second reception signals and a grip force calculation circuit configured to generate a grip force signal corresponding to the user's grip force based on the force signal.

16. The display device of claim 15, wherein the grip force calculation circuit further generates the grip force signal based on a value corresponding to the force signal, the value being stored in a memory.

17. The display device of claim 16, wherein the memory is a lookup table.

* * * * *